United States Patent
Park

(10) Patent No.: US 11,780,790 B2
(45) Date of Patent: Oct. 10, 2023

(54) ORGANIC LIGHT EMITTING DEVICE, CROSSLINKING AGENT COMPOUND FOR ORGANIC LIGHT EMITTING DEVICE AND MANUFACTURING METHOD OF THE ORGANIC LIGHT EMITTING DEVICE

(71) Applicant: Samsung Display Co., Ltd., Yongin-si (KR)

(72) Inventor: Junwoo Park, Daejeon (KR)

(73) Assignee: Samsung Display Co., Ltd., Yongin-si (KR)

( * ) Notice: Subject to any disclaimer, the term of this patent is extended or adjusted under 35 U.S.C. 154(b) by 234 days.

(21) Appl. No.: 17/248,436

(22) Filed: Jan. 25, 2021

(65) Prior Publication Data
US 2021/0347714 A1 Nov. 11, 2021

(30) Foreign Application Priority Data
May 6, 2020 (KR) .................. 10-2020-0054089

(51) Int. Cl.
C07C 11/21 (2006.01)
H10K 71/13 (2023.01)
(Continued)

(52) U.S. Cl.
CPC ............ C07C 11/21 (2013.01); H10K 71/135 (2023.02); H10K 85/141 (2023.02);
(Continued)

(58) Field of Classification Search
CPC .................................................. C07C 11/21
See application file for complete search history.

(56) References Cited

U.S. PATENT DOCUMENTS 6,814,887 B2  11/2004  Okunaka et al.
2016/0111656 A1*  4/2016  Ha .......................... C08F 26/02
                                                                526/310

FOREIGN PATENT DOCUMENTS

KR  10-1103488 B1  1/2012

OTHER PUBLICATIONS

Png, Rui-Qi et al.; "High-performance polymer semiconducting heterostructure devices by nitrene-mediated photocrosslinking of alkyl side chains"; *Nature Materials*; 2010; vol. 9, p. 152-158.
(Continued)

*Primary Examiner* — William D Young
(74) *Attorney, Agent, or Firm* — Lewis Roca Rothgerber Christie LLP

(57) ABSTRACT

An organic light emitting device of an embodiment of the present disclosure includes a first electrode, a hole transport region, an emission layer, an electron transport region, and a second electrode, stacked one by one, wherein the hole transport region includes a hole transport material derived from a crosslinking agent compound represented by Formula 1. The organic light emitting device may be manufactured through a wet process, and the emission efficiency and driving voltage properties of the organic light emitting device may be improved.

Formula 1

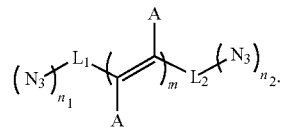

20 Claims, 3 Drawing Sheets

(51) Int. Cl.
  *H10K 85/10* (2023.01)
  *H10K 85/60* (2023.01)
  *H10K 50/15* (2023.01)
  *H10K 50/16* (2023.01)
  *H10K 50/18* (2023.01)
  *H10K 50/17* (2023.01)

(52) U.S. Cl.
  CPC ......... *H10K 85/615* (2023.02); *H10K 85/631* (2023.02); *H10K 50/15* (2023.02); *H10K 50/16* (2023.02); *H10K 50/171* (2023.02); *H10K 50/18* (2023.02)

(56) References Cited

OTHER PUBLICATIONS

Derue, Lionel et al.; "Thermal Stabilisation of Polymer-Fullerene Bulk Heterojunction Morphology for Efficient Photovoltaic Solar Cells"; *Advanced Materials*; 2014; 26; p. 5831-5838.

* cited by examiner

ORGANIC LIGHT EMITTING DEVICE, CROSSLINKING AGENT COMPOUND FOR ORGANIC LIGHT EMITTING DEVICE AND MANUFACTURING METHOD OF THE ORGANIC LIGHT EMITTING DEVICE

CROSS-REFERENCE TO RELATED APPLICATIONS

This application claims priority to and the benefit of Korean Patent Application No. 10-2020-0054089, filed on May 6, 2020, the entire content of which is incorporated herein by reference.

BACKGROUND

One or more aspects of embodiments of the present disclosure relate to an organic light emitting device and a crosslinking agent compound used therein, and for example, to a crosslinking agent compound used as a material for forming a hole transport region and an organic light emitting device including the same.

Organic electroluminescence displays are being actively developed as image displays. An organic electroluminescence display is different from a liquid crystal display and is so-called a self-luminescent display, in which holes and electrons respectively injected from a first electrode and a second electrode recombine in an emission layer, and an organic light emitting material in the emission layer may emit light to achieve display.

In display applications, a decrease in driving voltage and increase in emission efficiency and/or life span of the organic light emitting device are desired, and development of materials for an organic light emitting device stably attaining these requirements is continuously desired.

In order to accomplish an organic light emitting device with high efficiency, improved hole transport layer materials are being developed.

SUMMARY

One or more aspects of embodiments of the present disclosure are directed toward an organic light emitting device having improved emission efficiency and/or driving voltage properties.

One or more aspects of embodiments of the present disclosure are directed toward an organic light emitting device that may be manufactured utilizing a wet process and a crosslinking agent compound described herein.

One or more example embodiments of the present disclosure provide an organic light emitting device including a first electrode, a hole transport region disposed on the first electrode, an emission layer disposed on the hole transport region, an electron transport region disposed on the emission layer, and a second electrode disposed on the electron transport region, wherein at least a portion of the hole transport region is derived from (e.g., formed from) a hole transport material including a crosslinking agent compound represented by Formula 1:

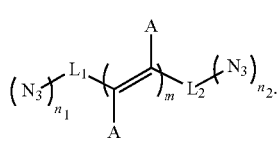

Formula 1

In Formula 1, A may be a hydrogen atom or a deuterium atom, $L_1$ and $L_2$ may each independently be a direct linkage, or a substituted or unsubstituted methylene group, "m" may be an integer of 1 to 100, and "$n_1$" and "$n_2$" may each independently be 1 or 2. "$N_3$" refers to an azide group.

In an embodiment, the hole transport region may include a hole injection layer disposed on the first electrode, and a hole transport layer disposed on the hole injection layer, and the hole transport layer may be derived from the hole transport material including the crosslinking agent compound represented by Formula 1.

In an embodiment, the hole transport region may include a plurality of organic layers, and an organic layer adjacent to (e.g., closest to or directly adjacent to) the emission layer among the plurality of organic layers may be derived from the hole transport material including the crosslinking agent compound represented by Formula 1.

In an embodiment, the crosslinking agent compound represented by Formula 1 may be represented by Formula 1-1 or Formula 1-2:

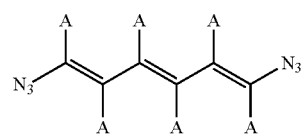

Formula 1-1

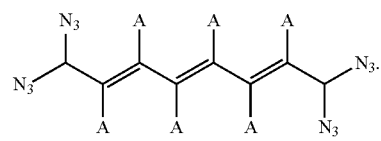

Formula 1-2

In Formula 1-1 and Formula 1-2, A may be the same as defined in Formula 1.

In an embodiment, the hole transport material may further include a polymer compound including a substituted or unsubstituted triarylamine group.

In an embodiment, the polymer compound may be represented by Formula 2-1 or Formula 2-2:

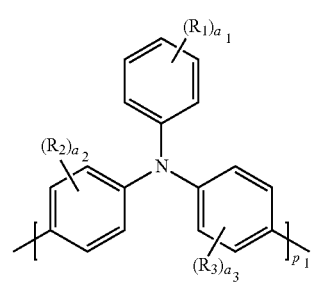

Formula 2-1

Formula 2-2

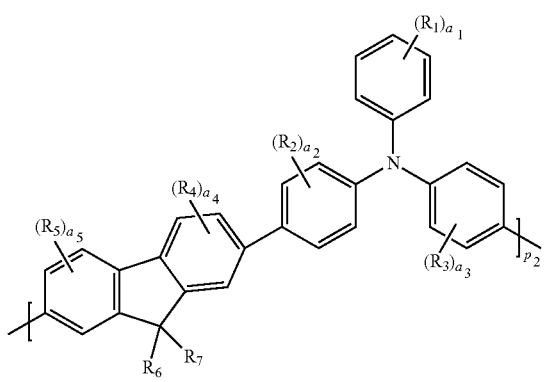

Formula 2-2-1

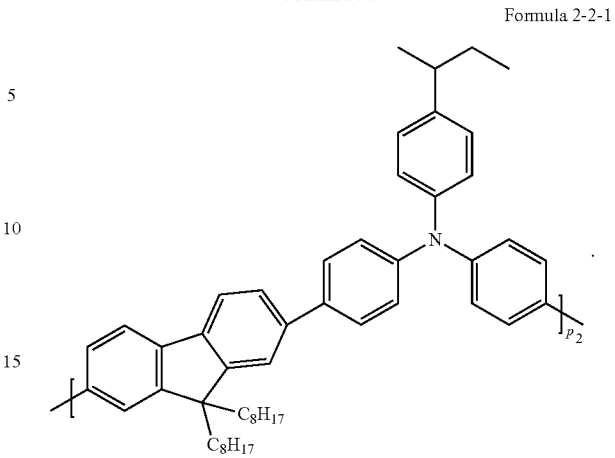

In Formula 2-1 and Formula 2-2, $R_1$ to $R_7$ may each independently be a hydrogen atom, a deuterium atom, a halogen atom, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring, "$a_1$" may be an integer of 0 to 5, "$a_2$" and "$a_3$" may each independently be an integer of 0 to 4, "$a_4$" and "$a_5$" may each independently be an integer of 0 to 3, and "$p_1$" and "$p_2$" may each independently be an integer of 1 to 100.

In an embodiment, the polymer compound may be represented by any one among Formula 2-1-1, Formula 2-1-2 and Formula 2-2-1:

Formula 2-1-1

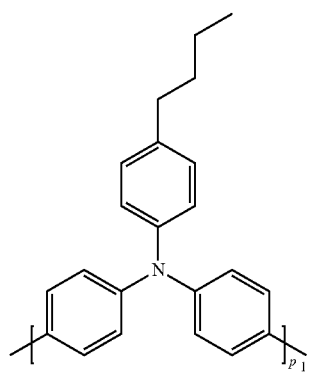

Formula 2-1-2

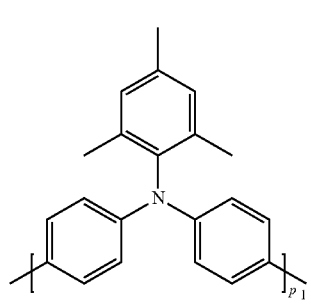

in Formula 2-1-1, Formula 2-1-2 and Formula 2-2-1, "$p_1$" and "$p_2$" may be the same as defined in Formula 2-1 and Formula 2-2.

In an embodiment, a weight ratio of the polymer compound and the crosslinking agent compound, included in the hole transport material may be about 4:1 to about 19:1.

In an embodiment, in the hole transport region, the polymer compound may be thermally-crosslinked or photo-crosslinked with the crosslinking agent compound.

In an embodiment of the present disclosure, a crosslinking agent compound according to an embodiment may be represented by Formula 1.

One or more example embodiments of the present disclosure provide a method of manufacturing an organic light emitting device including: preparing a first electrode, supplying a hole transport material on the first electrode to form a hole transport region, forming an emission layer on the hole transport region, and forming a second electrode on the emission layer, wherein the hole transport material includes a compound represented by Formula 1.

In the method of manufacturing an organic light emitting device according to an embodiment of the present disclosure, the hole transport layer may be formed through the hole transport material.

In an embodiment, the method may further include preparing the hole transport material by mixing the polymer compound, the crosslinking agent compound, and a solvent, prior to supplying the hole transport material on the first electrode.

In an embodiment, the forming of the hole transport region may further include curing the hole transport material supplied by applying heat or light, after supplying the hole transport material.

In an embodiment, the supplying of the hole transport material may be performed through a wet process such as spin coating, ink jet printing, nozzle printing, and spray printing.

BRIEF DESCRIPTION OF THE DRAWINGS

The accompanying drawings are included to provide a further understanding of the present disclosure, and are incorporated in and constitute a part of this specification. The drawings illustrate example embodiments of the present disclosure and, together with the description, serve to explain principles of the present disclosure. In the drawings.

DETAILED DESCRIPTION

Figure 1:
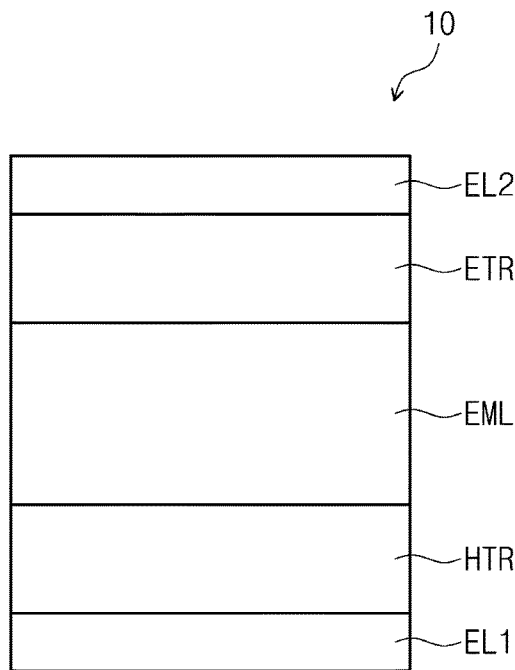
FIG. 1 is a cross-sectional view schematically illustrating an organic light emitting device according to an embodiment of the present disclosure.

The present disclosure may have various modifications and may be embodied in different forms, and example embodiments will be explained in more detail with reference to the accompany drawings. The present disclosure should not be construed as being limited to the embodiments set forth herein. Rather, all modifications, equivalents, and substituents in the spirit and technical scope of the inventive concept should be included in the present disclosure.

It will be understood that when an element is referred to as being "on", "connected to" or "coupled to" another element, it can be directly on, connected or coupled to the other element or intervening elements may be present. When an element is referred to as being "directly on," "directly connected to," or "directly coupled to" another element, there are no intervening elements present.

Like reference numerals refer to like elements throughout, and duplicative descriptions thereof may not be provided. In addition, the thickness, the ratio, and the dimensions of constituent elements in the drawings may be exaggerated for effective explanation of technical contents.

The term "and/or" includes one or more combinations which may be defined by relevant elements. As used herein, the singular forms "a," "an," and "the" are intended to include the plural forms as well, unless the context clearly indicates otherwise.

As used herein, expressions such as "at least one of," "one of," and "selected from," when preceding a list of elements, modify the entire list of elements and do not modify the individual elements of the list.

It will be understood that, although the terms first, second, etc. may be used herein to describe various elements, these elements should not be limited by these terms. These terms are only used to distinguish one element from another element. Thus, a first element could be termed a second element without departing from the teachings of the present disclosure. Similarly, a second element could be termed a first element. As used herein, the singular forms are intended to include the plural forms as well, unless the context clearly indicates otherwise.

In addition, the terms "below", "beneath", "on" and "above" are used for explaining the relation of elements shown in the drawings. The terms are relative concept and are explained on the basis of the direction shown in the drawing.

Unless otherwise defined, all terms (including technical and scientific terms) used herein have the same meaning as commonly understood by those of ordinary skill in the art to which the present disclosure pertains. It will be further understood that terms, such as those defined in commonly used dictionaries, should be interpreted as having meanings consistent with meanings in the context of the related art, unless expressly defined herein, and should not be interpreted in an ideal or overly formal sense.

It will be further understood that the terms "includes," "including," "comprises," and/or "comprising," when used in this specification, specify the presence of stated features, numerals, steps, operations, elements, parts, or the combination thereof, but do not preclude the presence or addition of one or more other features, numerals, steps, operations, elements, parts, or the combination thereof.

Hereinafter, the organic light emitting device according to an embodiment of the present disclosure will be explained with reference to attached drawings.

Figure 2:
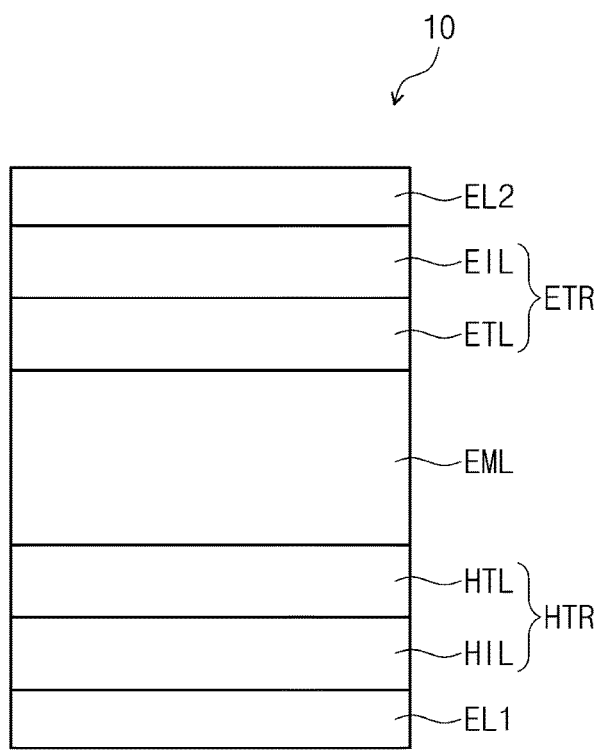
FIG. 2 is a cross-sectional view schematically illustrating an organic light emitting device according to an embodiment of the present disclosure.
Figure 3:
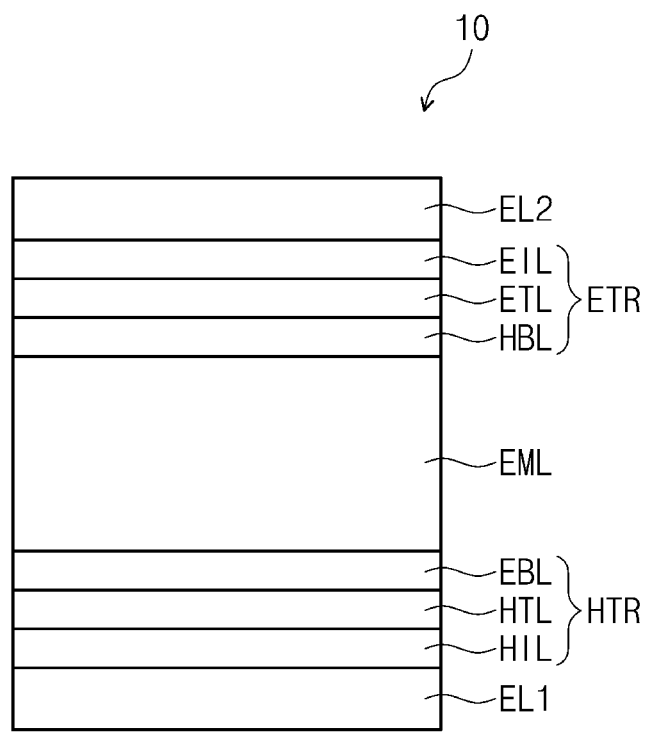
FIG. 3 is a cross-sectional view schematically illustrating an organic light emitting device according to an embodiment of the present disclosure.

FIG. 1 to FIG. 3 are cross-sectional views schematically showing organic light emitting devices according to example embodiments of the present disclosure. Referring to FIGS. 1 to 3, in an organic light emitting device 10 according to an embodiment, a first electrode EL1 and a second electrode EL2 are oppositely disposed, and between the first electrode EL1 and the second electrode EL2, a plurality of organic layers may be disposed. The plurality of organic layers may include a hole transport region HTR, an emission layer EML, and an electron transport region ETR. For example, the organic light emitting device 10 according to an embodiment may include a first electrode EL1, a hole transport region HTR, an emission layer EML, an electron transport region ETR, and a second electrode EL2, stacked one by one. In some embodiments, a capping layer may be further disposed on the second electrode EL2.

The organic light emitting device 10 of an embodiment may include a crosslinking agent compound of an embodiment, which will be explained later, in at least one layer among the plurality of organic layers disposed between the first electrode EL1 and the second electrode EL2. For example, the organic light emitting device 10 of an embodiment may include the crosslinking agent compound of an embodiment in the hole transport region HTR disposed between the first electrode EL1 and the second electrode EL2. However, embodiments of the present disclosure are not limited thereto. The organic light emitting device 10 of an embodiment may include the crosslinking agent compound of an embodiment in at least one layer included in an emission layer EML and an electron transport region ETR (which are among the plurality of organic layers disposed between the first electrode EL1 and the second electrode EL2), or may include the crosslinking agent compound of an embodiment in a functional layer such as the capping layer disposed on the second electrode EL2.

Compared with FIG. 1, FIG. 2 shows the cross-sectional view of an organic light emitting device 10 of an embodiment, wherein the hole transport region HTR includes a hole injection layer HIL and a hole transport layer HTL, and the electron transport region ETR includes an electron injection layer EIL and an electron transport layer ETL. Compared with FIG. 1, FIG. 3 shows the cross-sectional view of an organic light emitting device 10 of an embodiment, wherein the hole transport region HTR includes the hole injection layer HIL, the hole transport layer HTL, and an electron blocking layer EBL, and the electron transport region ETR includes the electron injection layer EIL, the electron transport layer ETL, and a hole blocking layer HBL.

The first electrode EL1 has conductivity. The first electrode EL1 may be formed using a metal alloy or a conductive compound. The first electrode EL1 may be an anode. In addition, the first electrode EL1 may be a pixel electrode. The first electrode EL1 may be a transmissive electrode, a transflective electrode, or a reflective electrode. When the first electrode EL1 is a transmissive electrode, the first electrode EL1 may be formed using a transparent metal oxide (such as indium tin oxide (ITO), indium zinc oxide (IZO), zinc oxide (ZnO), and/or indium tin zinc oxide (ITZO)). When the first electrode EL1 is a transflective electrode or a reflective electrode, the first electrode EL1 may include silver (Ag), magnesium (Mg), copper (Cu), aluminum (Al), platinum (Pt), palladium (Pd), gold (Au), nickel (Ni), neodymium (Nd), iridium (Ir), chromium (Cr), lithium (Li), calcium (Ca), LiF/Ca, LiF/Al, molybdenum (Mo), titanium (Ti), tungsten (W), indium (In), tin (Sn), zinc (Zn), compounds thereof, mixtures thereof (for example, a mixture of Ag and Mg), or oxides of one or more thereof. In some embodiments, the first electrode EL1 may have a structure including a plurality of layers including a reflective layer or a transflective layer formed using the above materials, and a transmissive conductive layer formed using ITO, IZO, ZnO, or ITZO. For example, the first electrode EL1 may include a three-layer structure of ITO/Ag/ITO.

However, embodiments of the present disclosure are not limited thereto. The thickness of the first electrode EL1 may be about 1,000 Å to about 10,000 Å, for example, about 1,000 Å to about 3,000 Å.

The hole transport region HTR may be provided on the first electrode EL1. The hole transport region HTR may include at least one of a hole injection layer HIL, a hole transport layer HTL, a hole buffer layer, or an electron blocking layer EBL. The thickness of the hole transport region HTR may be about 50 Å to about 1500 Å.

The hole transport region HTR may have (include) a single layer formed using a single material, a single layer formed using a plurality of different materials, or a multi-layer structure including a plurality of layers formed using a plurality of different materials.

For example, the hole transport region HTR may have the structure of a single layer of a hole injection layer HIL or a hole transport layer HTL, or may have a structure of a single layer formed using a hole injection material and a hole transport material. In some embodiments, the hole transport region HTR may have a structure of a single layer formed using a plurality of different materials, or a structure stacked from the first electrode EL1 of hole injection layer HIL/hole transport layer HTL, hole injection layer HIL/hole transport layer HTL/hole buffer layer, hole injection layer HIL/hole buffer layer, hole transport layer HTL/hole buffer layer, or hole injection layer HIL/hole transport layer HTL/electron blocking layer EBL, but an embodiment of the present disclosure is not limited thereto.

The hole transport region HTR may be formed using any suitable method (such as a vacuum deposition method, a spin coating method, a cast method, a Langmuir-Blodgett (LB) method, an inkjet printing method, a laser printing method, and/or a laser induced thermal imaging (LITI) method).

The hole transport region HTR in the organic light emitting device 10 of an embodiment may include the crosslinking agent compound of an embodiment. In the organic light emitting device 10 of an embodiment, the hole transport region HTR may be derived from (e.g., formed from) a hole transport material (HTM, see FIG. 4A) including the crosslinking agent compound of an embodiment.

In the description, the term "substituted or unsubstituted" refers to a state of being unsubstituted, or substituted with at least one substituent selected from the group consisting of a deuterium atom, a halogen atom, a cyano group, a nitro group, an amino group, a silyl group, an oxy group, a thio group, a sulfinyl group, a sulfonyl group, a carbonyl group, a boron group, a phosphine oxide group, a phosphine sulfide group, an alkyl group, an alkenyl group, an alkoxy group, a hydrocarbon ring group, an aryl group, and a heterocyclic group. In addition, each of the above substituents may be further substituted, or unsubstituted. For example, a biphenyl group may be interpreted as a named aryl group, or as a phenyl group substituted with a phenyl group.

In the description, the term "forming a ring via the combination with an adjacent group" may refer to forming a substituted or unsubstituted hydrocarbon ring, or a substituted or unsubstituted heterocycle via combination with an adjacent group. The hydrocarbon ring may be an aliphatic hydrocarbon ring or an aromatic hydrocarbon ring. The heterocycle may be an aliphatic heterocycle or an aromatic heterocycle. The ring formed by combination with an adjacent group may be a monocyclic ring or a polycyclic ring. In addition, the ring formed via combination with an adjacent group may be combined with another ring to form a spiro structure.

In the description, the term "adjacent group" may refer to a substituent on the same atom or point, a substituent on an atom that is directly connected to the base atom or point, or a substituent sterically positioned (e.g., within intramolecular bonding distance) to the corresponding substituent. For example, in 1,2-dimethylbenzene, two methyl groups may be interpreted as "adjacent groups" to each other, and in 1,1-diethylcyclopentane, two ethyl groups may be interpreted as "adjacent groups" to each other.

In the description, the term "direct linkage" may refer to a single bond.

In the description, the halogen atom may be a fluorine atom, a chlorine atom, a bromine atom, or an iodine atom.

In the description, the term "alkyl group" may refer to a linear chain, a branched chain, or a cyclic alkyl group. The carbon number of the alkyl may be 1 to 50, 1 to 30, 1 to 20, 1 to 10, or 1 to 6. Examples of the alkyl group include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldocecyl, 2-octyldodecyl, n-tridecyl, n-tetradecyl, n-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyleicosyl, 2-butyleicosyl, 2-hexyleicosyl, 2-octyleicosyl, n-henicosyl, n-docosyl, n-tricosyl, n-tetracosyl, n-pentacosyl, n-hexacosyl, n-heptacosyl, n-octacosyl, n-nonacosyl, n-triacontyl, etc., without limitation.

In the description, the hydrocarbon ring may be an aliphatic hydrocarbon ring or an aromatic heterocycle. The heterocycle may be an aliphatic heterocycle and an aromatic heterocycle. The hydrocarbon ring and the heterocycle may be a monocycle or a polycycle.

In the description, the hydrocarbon ring group may be an optional functional group derived from an aliphatic hydrocarbon ring, or an optional functional group or substituent derived from an aromatic hydrocarbon ring. The hydrocarbon ring group may have 5 to 60 carbon atoms for forming a ring.

In the description, the heterocycle may be an optional functional group or substituent derived from a heterocycle including at least one heteroatom as a ring-forming atom. The heterocycle may have 5 to 60 carbon atoms for forming a ring.

In the description, the term "aryl group" refers to an optional functional group or substituent derived from an aromatic hydrocarbon ring. The aryl group may be a monocyclic aryl group or a polycyclic aryl group. The carbon number for forming a ring in the aryl group may be 6 to 30, 6 to 20, or 6 to 15. Examples of the aryl group may include phenyl, naphthyl, fluorenyl, anthracenyl, phenanthryl, biphenyl, terphenyl, quaterphenyl, quinquephenyl, sexiphenyl, triphenylenyl, pyrenyl, benzofluoranthenyl, chrysenyl, etc., without limitation.

In the description, the fluorenyl group may be substituted (e.g., at the 9H position), and two substituents may be combined with each other to form a spiro structure. Examples of a substituted fluorenyl group are as follows. However, embodiments of the present disclosure are not limited thereto.

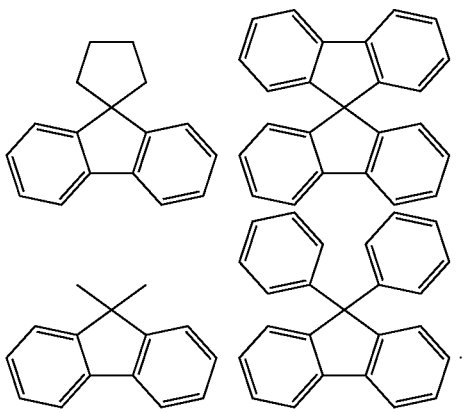

In the description, the heteroaryl group may include one or more among B, O, N, P, Si and S as heteroatoms. When the heteroaryl group includes two or more heteroatoms, the two or more heteroatoms may be the same or different. The heteroaryl group may be a monocyclic heterocyclic group or a polycyclic heterocyclic group. The carbon number for forming a ring of the heteroaryl group may be 2 to 30, 2 to 20, or 2 to 10. Examples of the heteroaryl group include thiophene, furan, pyrrole, imidazole, thiazole, oxazole, oxadiazole, triazole, pyridine, bipyridine, pyrimidine, triazine, triazole, acridyl, pyridazine, pyrazinyl, quinoline, quinazoline, quinoxaline, phenoxazine, phthalazine, pyrido pyrimidine, pyrido pyrazine, pyrazino pyrazine, isoquinoline, indole, carbazole, N-arylcarbazole, N-heteroarylcarbazole, N-alkylcarbazole, benzoxazole, benzimidazole, benzothiazole, benzocarbazole, benzothiophene, dibenzothiophene, thienothiophene, benzofuran, phenanthroline, thiazole, isooxazole, oxadiazole, thiadiazole, phenothiazine, dibenzosilole, dibenzofuran, etc., without limitation.

In the description, the explanation of the aryl group may be applied to the arylene group, except that the arylene group is a divalent group. The explanation of the heteroaryl group may be applied to the heteroarylene group, except that the heteroarylene group is a divalent group.

In the description, the term "alkenyl group" may refer to a linear chain or a branched chain alkenyl group. The carbon number is not specifically limited but may be 2 to 30, 2 to 20, or 2 to 10. Examples of the alkenyl group include a vinyl group, a 1-butenyl group, a 1-pentenyl group, a 1,3-butadienyl aryl group, a styrenyl group, a styrylvinyl group, etc., without limitation.

In the description, the term "silyl group" may refer to an alkyl silyl group or an aryl silyl group. Examples of the silyl group include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, etc., without limitation.

In the description, the term "boron group" may refer to an alkyl boron group and an aryl boron group. Examples of the boron group include a trimethylboron group, a triethylboron group, a t-butyldimethylboron group, a triphenylboron group, a diphenylboron group, a phenylboron group, etc., without limitation.

In the description, the carbon number of the amine group is not specifically limited, but may be 1 to 30. The amine group may be an alkyl amine group or an aryl amine group. Examples of the amine group include a methylamine group, a dimethylamine group, a phenylamine group, a diphenylamine group, a naphthylamine group, a 9-methyl-anthracenylamine group, a triphenylamine group, etc., without limitation.

In the description, the term "hydrocarbon ring group" refers to an optional functional group or substituent derived from an aliphatic hydrocarbon ring. The hydrocarbon ring group may be a saturated hydrocarbon ring group of 5 to 20 carbon atoms for forming a ring.

In the description, the heterocyclic group may include one or more among B, O, N, P, Si and S as heteroatoms. When the heterocyclic group includes two or more heteroatoms, the two or more heteroatoms may be the same or different. The heterocyclic group may be a monocyclic heterocyclic group or a polycyclic heterocyclic group, and in some embodiments, it may be a heteroaryl group. The carbon number for forming a ring of the heterocyclic group may be 2 to 30, 2 to 20, or 2 to 10.

In the description, "-*" indicates a connected position.

The crosslinking agent compound includes a bis-azide structure, e.g., including two azide groups, and a polyacetylene (PA) group as a main chain. The crosslinking agent compound of an embodiment may include a connected structure of two azide groups at both sides (e.g., two ends) of a polyacetylene main chain.

The crosslinking agent compound of an embodiment may be represented by Formula 1:

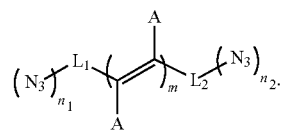

Formula 1

In Formula 1, A may be a hydrogen atom or a deuterium atom. In Formula 1, a plurality of A may be the same or different. In some embodiments, all A may be hydrogen atoms. In some embodiments, at least one of the plurality of A may be a deuterium atom, and the remainder may be hydrogen atoms. The crosslinking agent compound represented by Formula 1 may include an acetylene group as a main chain, which may be unsubstituted (e.g., may not include any substituents other than hydrogen atoms or deuterium atoms).

In Formula 1, $L_1$ and $L_2$ may each independently be a direct linkage, or a substituted or unsubstituted methylene group. In an embodiment, $L_1$ and $L_2$ may be the same or different. For example, both $L_1$ and $L_2$ may be direct linkages or unsubstituted methylene groups.

In Formula 1, "m" may be an integer of 1 to 100. When "m" is an integer of 2 or more, the main chain of the compound includes multiple repeats of an acetylene group. For example, when "m" is an integer of 2 or more, a plurality of acetylene groups may be repeatedly connected (e.g., in a row). In an embodiment, "m" may be an integer of 3 to 20.

In Formula 1, "$n_1$" and "$n_2$" may each independently be 1 or 2. When "$n_1$" and "$n_2$" are each 1, two azide groups are present, with one on each side of the main chain. In an embodiment, "$n_1$" and "$n_2$" may be the same or different. For example, "$n_1$" and "$n_2$" may both be 1 or 2.

The crosslinking agent compound of an embodiment has a structure in which one pair or two pairs of azide groups are connected (present) at both sides (ends) of a polyacetylene chain (which is a main chain of the compound). The crosslinking agent compound of an embodiment may have a structure in which bis-azide groups are connected at both sides with a central polyacetylene main chain that is substituted only with hydrogen or deuterium atoms, and the crosslinking efficiency may be improved without reducing the hole transport capacity of a polymer compound included in a hole transport region. Accordingly, an organic light emitting device including the crosslinking agent compound of an embodiment may have improved resolution, high emission efficiency, and a low driving voltage when the hole transport region is formed through a wetting process such as ink jet printing.

The crosslinking agent compound according to an embodiment of the present disclosure may be represented by Formula 1-a:

Formula 1-a

In Formula 1-a, A and "m" may be the same as described in connection with to Formula 1.

In Formula 1-a, B may be represented by Formula 1-b or Formula 1-c:

Formula 1-b

Formula 1-c

In Formula 1-b and Formula 1-c, -* indicates a connecting portion with the acetylene main chain represented in Formula 1-a.

In Formula 1-a, the two B groups connected at both sides of the acetylene main chain may be the same or different. In an embodiment, both B groups may be represented by Formula 1-b. In an embodiment, both B groups may be represented by Formula 1-c.

The crosslinking agent compound according to an embodiment of the present disclosure may be represented by Formula 1-1 or Formula 1-2:

Formula 1-1

Formula 1-2

Formula 1-1 corresponds to an embodiment of Formula 1, where "m" is 3, both $L_1$ and $L_2$ are direct linkages, and both $n_1$ and $n_2$ are 1. Formula 1-2 corresponds to an embodiment of Formula 1, where "m" is 3, both $L_1$ and $L_2$ are unsubstituted methylene groups, and both $n_1$ and $n_2$ are 2.

In Formula 1-1 and Formula 1-2, A may be the same as described in connection with Formula 1 may be applied.

In the organic light emitting device 10 of an embodiment, the hole transport region HTR may further include a polymer compound having hole transport properties (e.g., capacity) in addition to the crosslinking agent compound of an embodiment. The polymer compound may include a substituted or unsubstituted triarylamine group. The polymer compound may include or be formed from a monomer including the substituted or unsubstituted triarylamine group as a repeating unit.

The polymer compound according to an embodiment may be represented by Formula 2-1 or Formula 2-2. For example, the polymer compound according to an embodiment may be a polymer including a monomer represented by Formula 2-1 or Formula 2-2 as a repeating unit.

Formula 2-1

Formula 2-2

In Formula 2-1 and Formula 2-2, $R_1$ to $R_7$ may each independently be a hydrogen atom, a deuterium atom, a halogen atom, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring. In an embodiment, $R_1$ to $R_7$ may each independently be a hydrogen atom, or a substituted or unsubstituted alkyl group of 1 to 8 carbon atoms. For example, $R_1$ may be a hydrogen atom, a substituted or unsubstituted methyl group, or a substituted or unsubstituted butyl group. For example, $R_6$ and $R_7$ may be each independently a substituted or unsubstituted octyl group.

In Formula 2-1 and Formula 2-2, "$a_1$" may be an integer of 0 to 5. "$a_2$" and "$a_3$" may each independently be an integer of 0 to 4. "$a_4$" and "$a_5$" may each independently be an integer of 0 to 3. When each of "$a_1$" to "$a_5$" is 0, in the polymer compound according to an embodiment, each of $R_1$ to $R_5$ may be a hydrogen atom. When each of "$a_1$" to "$a_5$" is an integer of 2 or more, a plurality of $R_1$ to $R_5$ may be the same or different.

In Formula 2-1 and Formula 2-2, "$p_1$" and "$p_2$" may each independently be an integer of 1 to 100. In an embodiment, a case where each of "$p_1$" and "$p_2$" is an integer of 2 or more corresponds to a case where a plurality of monomers represented by Formula 2-1 and Formula 2-2 is provided. For example, a case where each of "$p_1$" and "$p_2$" is an integer of 2 or more corresponds to a case where a plurality of monomers represented in Formula 2-1 and Formula 2-2 are repeatedly connected. In an embodiment, each of "$p_1$" and "$p_2$" may be an integer of 3 to 20.

The polymer compound according to an embodiment may be represented by Formula 2-1-1, Formula 2-1-2 or Formula 2-2-1:

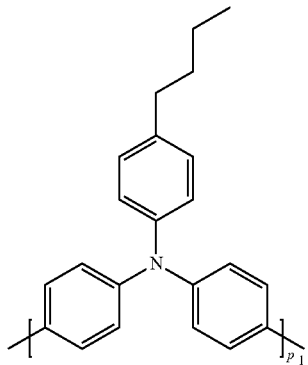

Formula 2-1-1

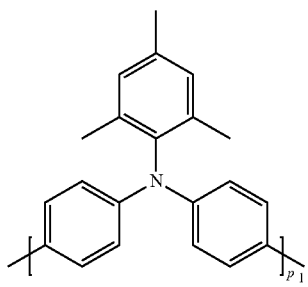

Formula 2-1-2

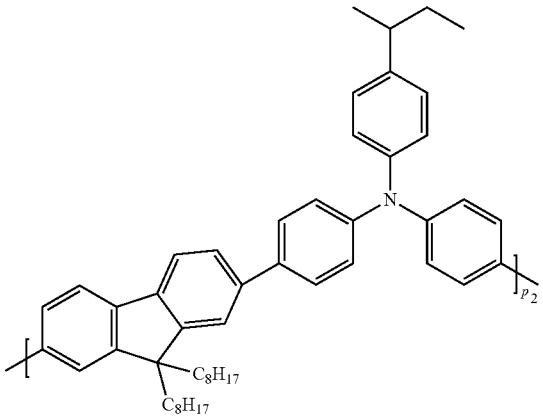

Formula 2-2-1

Formula 2-1-1, Formula 2-1-2 and Formula 2-2-1 are example embodiments of Formula 2-1 and Formula 2-2 in which the substituents indicated by $R_1$ to $R_7$ are specified.

In Formula 2-1-1, Formula 2-1-2 and Formula 2-2-1, "$p_1$" and "$p_2$" may be the same as described in connection with Formula 1.

The crosslinking agent compound according to an embodiment and the polymer compound may each independently be included in a hole transport layer HTL in a hole transport region HTR. The weight ratio of the polymer compound and the crosslinking agent compound included in the hole transport layer HTL may be about 4:1 to about 19:1. In some embodiments, the weight ratio of the polymer compound and the crosslinking agent compound included in the hole transport layer HTL may be about 9:1. The polymer compound included in the hole transport layer HTL may be thermally-crosslinked or photo-crosslinked through the crosslinking agent compound.

In the organic light emitting device 10 of an embodiment, the hole transport region HTR may further include any suitable material.

The hole injection layer HIL may include, for example, a phthalocyanine compound (such as copper phthalocyanine), N,N'-diphenyl-N,N'-bis-[4-(phenyl-m-tolyl-amino)-phenyl]-biphenyl-4,4'-diamine (DNTPD), 4,4',4"-[tris(3-methylphenyl)phenylamino] triphenylamine (m-MTDATA), 4,4',4"-tris(N,N-diphenylamino)triphenylamine (TDATA), 4,4',4"-tris{N,-2-naphthyl)-N-phenylamino}-triphenylamine (2-TNATA), poly(3,4-ethylene dioxythiophene)/poly(4-styrene sulfonate) (PEDOT/PSS), polyaniline/dodecylbenzene sulfonic acid (PANI/DBSA), polyaniline/camphor sulfonic acid (PANI/CSA), polyaniline/poly(4-styrene sulfonate) (PANI/PSS), N,N'-di(1-naphthalene-1-yl)-N,N'-diphenyl-benzidine (NPB), triphenylamine-containing polyether ketone (TPAPEK), 4-isopropyl-4'-methyldiphenyliodonium [tetrakis(pentafluorophenyl)borate], and dipyrazino[2,3-f:2',3'-h]quinoxaline-2,3,6,7,10,11-hexacarbonitrile (HAT-CN).

In some embodiments, the hole transport layer HTL may further include, in addition to the crosslinking agent compound and the polymer compound, carbazole derivatives (such as N-phenyl carbazole and/or polyvinyl carbazole), fluorene-based derivatives, N,N'-bis(3-methylphenyl)-N,N'-diphenyl-[1,1-biphenyl]-4,4'-diamine (TPD), triphenylamine-based derivatives (such as 4,4',4"-tris(N-carbazolyl)triphenylamine (TCTA)), N,N'-di(1-naphthalen-1-yl)-N,N'-diphenyl-benzidine (NPB), 4,4'-cyclohexylidene bis[N,N-bis(4-methylphenyl)benzenamine (TAPC), 4,4'-bis[N,N'-(3- tolyl)amino]-3,3'-dimethylbiphenyl (HMTPD), 1,3-bis(N-carbazolyl)benzene (mCP), etc.

The thickness of the hole transport region HTR may be about 50 Å to about 10,000 Å, for example, about 100 Å to about 5,000 Å. The thickness of the hole injection layer HIL may be, for example, about 30 Å to about 1,000 Å, and the thickness of the hole transport layer HTL may be about 30 Å to about 1,000 Å. For example, the thickness of the electron blocking layer EBL may be about 10 Å to about 1,000 Å. When the thicknesses of the hole transport region HTR, the hole injection layer HIL, the hole transport layer HTL and the electron blocking layer EBL satisfy the above-described ranges, satisfactory hole transport properties may be achieved without substantial increase of a driving voltage.

The hole transport region HTR may further include a charge generating material in addition to the above-described materials to increase conductivity. The charge generating material may be dispersed substantially uniformly or non-uniformly in the hole transport region HTR. The charge generating material may be, for example, a p-dopant. The p-dopant may be selected from quinone derivatives, metal oxides, and cyano group-containing compounds, without limitation. For example, the p-dopant may include quinone derivatives (such as tetracyanoquinodimethane (TCNQ) and/or 2,3,5,6-tetrafluoro-7,7',8,8'-tetracyanoquinodimethane (F4-TCNQ)), metal oxides (such as tungsten oxide and/or molybdenum oxide), without limitation.

As described above, the hole transport region HTR may further include at least one of a hole buffer layer and an electron blocking layer EBL in addition to the hole injection layer HIL and the hole transport layer HTL. The hole buffer layer may compensate for an optical resonance distance of the wavelength of light emitted from an emission layer EML, and may thereby increase the light emission efficiency of the device. The materials that may be included in a hole transport region HTR may be included in a hole buffer layer. The electron blocking layer may prevent or reduce electron injection from the electron transport region ETR to the hole transport region HTR. When the hole transport region HTR includes at least one selected from a hole buffer layer and an electron blocking layer, adjacent to an emission layer EML, the crosslinking agent compound according to an embodiment may be included in the hole buffer layer and/or electron blocking layer, adjacent to an emission layer EML. In addition, the polymer compound according to an embodiment (included in the hole buffer layer and/or the electron blocking layer, adjacent to the emission layer EML) may be thermally-crosslinked or photo-crosslinked by the crosslinking agent compound.

The emission layer EML is provided on the hole transport region HTR. The emission layer EML may have a thickness of, for example, about 100 Å to about 1,000 Å or about 100 Å to about 300 Å. The emission layer EML may have a single layer formed using a single material, a single layer formed using a plurality of different materials, or a multi-layer structure having a plurality of layers formed using a plurality of different materials.

In addition, the emission layer EML of the organic light emitting device 10 may be to emit blue light. For example, the emission layer EML of the organic light emitting device 10 of an embodiment may emit blue light in a region of about 490 nm or more. However, an embodiment of the present disclosure is not limited thereto, but may be to emit green light or red light.

In some embodiments, the organic light emitting device 10 of an embodiment may include a plurality of emission layers. The plurality of emission layers may be stacked one by one, and for example, the organic light emitting device 10 including a plurality of emission layers may be to emit white light. The organic light emitting device including a plurality of emission layers may be an organic light emitting device having a tandem structure.

In an embodiment, the emission layer EML may be a delayed fluorescence emission layer, a fluorescence emission layer, a phosphorescence emission layer, etc., and the emission layer EML may include any suitable host material and a dopant. For example, the emission layer EML may be to emit thermally activated delayed fluorescence (TADF).

As the host material of the emission layer EML, any suitable material may be used and may be selected from fluoranthene derivatives, pyrene derivatives, arylacetylene derivatives, anthracene derivatives, fluorene derivatives, perylene derivatives, chrysene derivatives, etc., without specific limitation. In some embodiments, pyrene derivatives, perylene derivatives, and anthracene derivatives may be used. For example, as the host material of the emission layer EML, anthracene derivatives represented by Formula 3 may be used:

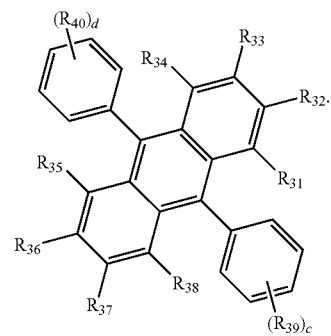

Formula 3 in Formula 3, $R_{31}$ to $R_{40}$ may each independently be a hydrogen atom, a deuterium atom, a halogen atom, a substituted or unsubstituted silyl group, a substituted or unsubstituted alkyl group of 1 to 10 carbon atoms, a substituted or unsubstituted aryl group of 6 to 30 carbon atoms for forming a ring, or a substituted or unsubstituted heteroaryl group of 2 to 30 carbon atoms for forming a ring, or combined with an adjacent group to form a ring. In some embodiments, $R_{31}$ to $R_{40}$ may be combined with an adjacent group to form a ring.

In Formula 3, "c" and "d" may each independently be an integer of 0 to 5.

Formula 3 may be represented by any one among Compound 3-1 to Compound 3-16:

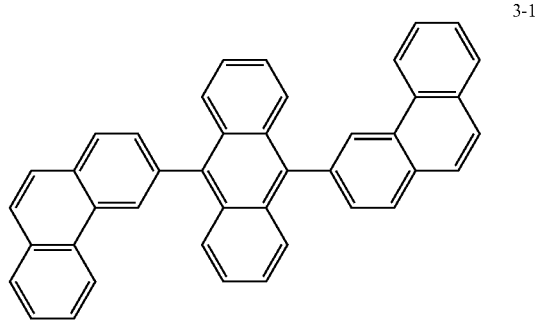

3-1

3-2
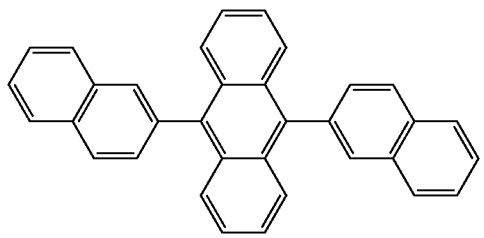
3-3
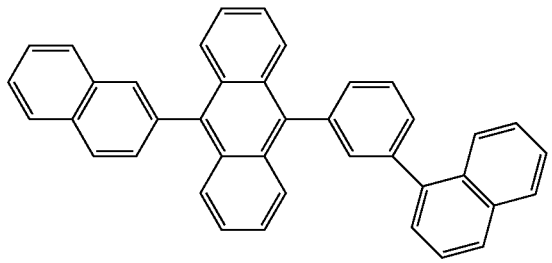
3-4
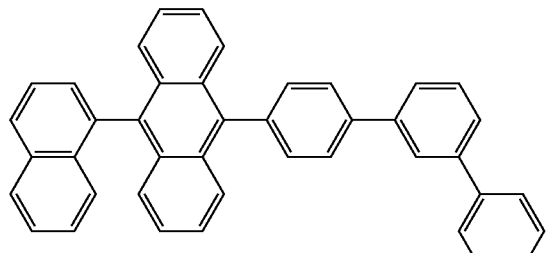
3-5
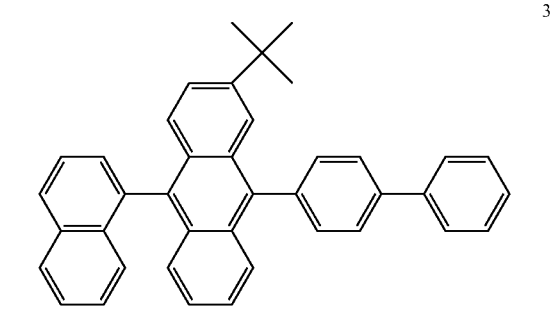
3-6
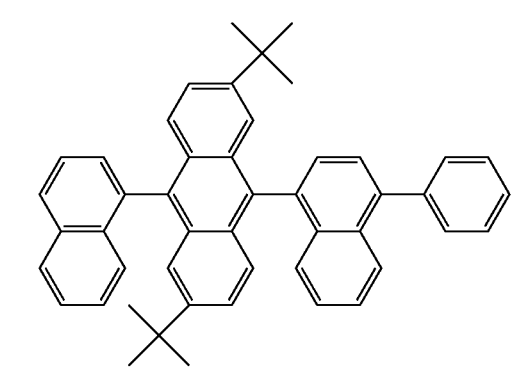
3-7
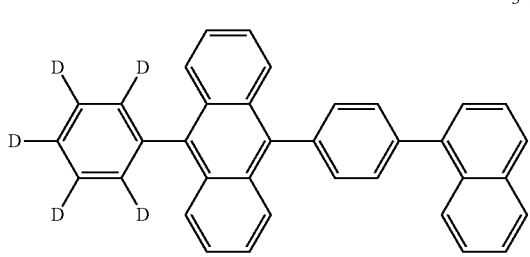
3-8
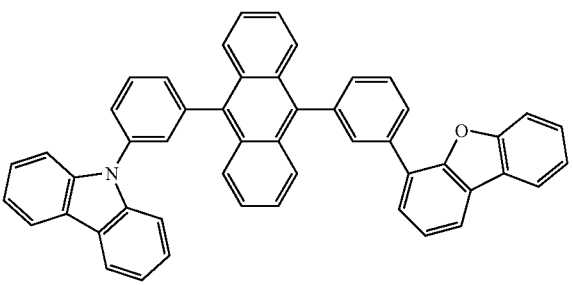
3-9
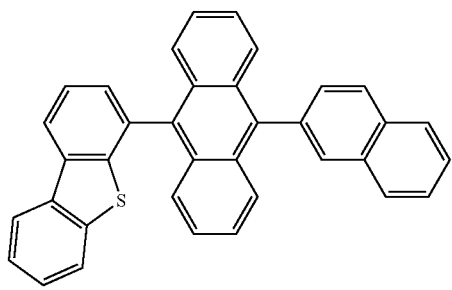
3-10
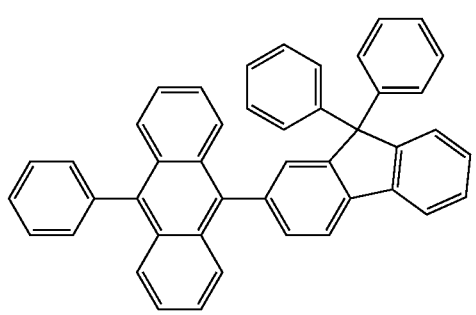
3-11
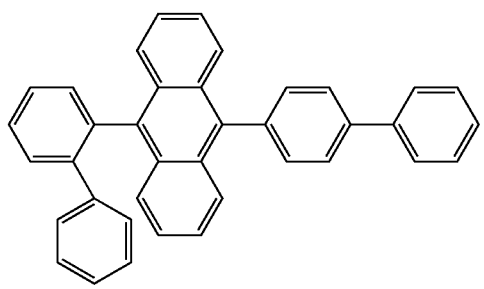

3-12

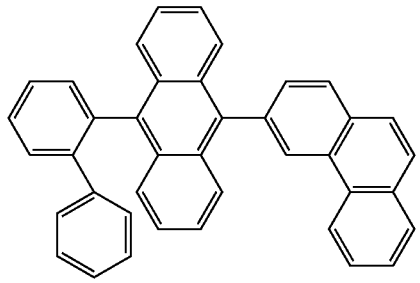

3-13

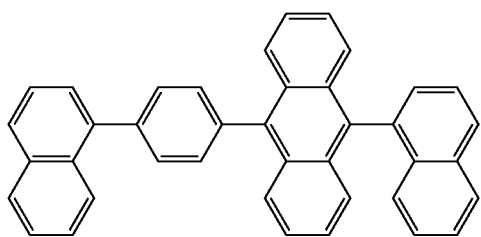

3-14

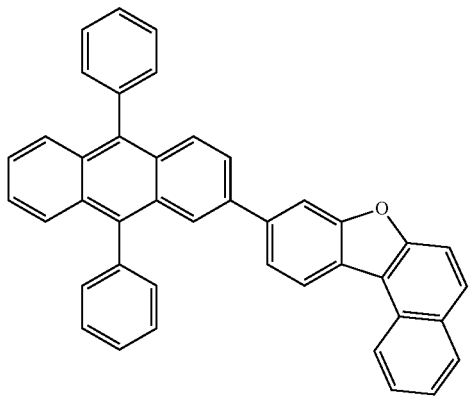

3-15

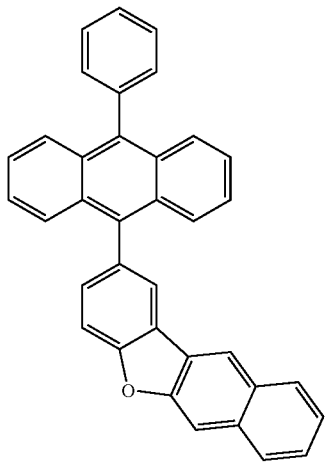

3-16

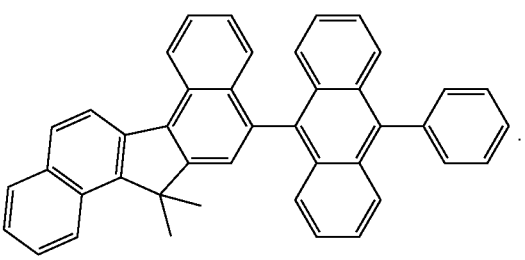

In an embodiment, the emission layer EML may include, as a host material, tris(8-hydroxyquinolinato)aluminum ($Alq_3$), 4,4'-bis(carbazolyl)-1,1'-biphenyl (CBP), poly(n-vinylcarbazole) (PVK), 9,10-di(naphthalene-2-yl)anthracene (ADN), 4,4',4''-tris(carbazol-9-yl)-triphenylamine (TCTA), 1,3,5-tris(1-phenyl-1H-benzo[d]imidazole-2-yl)benzene (TPBi), 3-tert-butyl-9,10-di(naphth-2-yl)anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), bis[2-(diphenylphosphino)phenyl]ether oxide (DPEPO), hexaphenyl cyclotriphosphazene (CP1), 1,4-bis(triphenylsilyl)benzene (UGH2), hexaphenylcyclotrisiloxane ($DPSiO_3$), octaphenylcyclotetrasiloxane ($DPSiO_4$), 2,8-bis(diphenylphosphoryl)dibenzofuran (PPF), 3,3'-bis(N-carbazolyl)-1,1'-biphenyl (mCBP), 1,3-bis(N-carbazolyl)benzene (mCP), 9,10-di(naphthalene-2-yl)anthracene (DNA), etc. However, embodiments of the present disclosure are not limited thereto, and any suitable delayed fluorescence emitting host material may be included in addition to the suggested host materials.

In an embodiment, the emission layer EML may include as a dopant, styryl derivatives (for example, 1,4-bis[2-(3-N-ethylcarbazolyl)vinyl]benzene (BCzVB), 4-(di-p-tolylamino)-4'-[(di-p-tolylamino)styryl]stilbene (DPAVB), and/or N-(4-((E)-2-(6((E)-4-(diphenylamino)styryl)naphthalen-2-yl)vinyl)phenyl)-N-phenylbenzenamine (N-BDAVBi)), perylene and derivatives thereof (for example, 2,5,8,11-tetra-t-butylperylene (TBP)), pyrene and derivatives thereof (for example, 1,1-dipyrene, 1,4-dipyrenylbenzene and/or 1,4-bis(N,N-diphenylamino)pyrene), etc.

In some embodiments, the emission layer EML may include two dopant materials having different lowest triplet excitation energy levels (T1 levels). In the organic light emitting device 10 of an embodiment, the emission layer EML may include a host having a first lowest triplet excitation energy level, a first dopant having a second lowest triplet excitation energy level that is lower than the first lowest triplet excitation energy level, and a second dopant having a third lowest triplet excitation energy level that is lower than the second lowest triplet excitation energy level.

In the organic light emitting device 10 of an embodiment, including the host, the first dopant, and the second dopant in the emission layer EML, the first dopant may be a delayed fluorescence dopant, and the second dopant may be a fluorescence dopant.

For example, when the emission layer EML of the organic light emitting device 10 of an embodiment includes a plurality of dopants, the emission layer EML may include a first dopant and a second dopant, which are different from each other. For example, when the emission layer EML is to emit blue light, the emission layer EML may further include any one selected from the group consisting of spiro-DPVBi, spiro-6P, distyryl-benzene (DSB), distyryl-arylene (DSA), a polyfluorene (PFO)-based polymer, and a poly(p-phenylene vinylene (PPV)-based polymer. In addition, as the second dopant, a metal or organometallic complex such as (4,6-$F_2$ppy)$_2$Irpic, or perylene and derivatives thereof may be used.

In the organic light emitting devices 10 of an embodiment, as shown in FIG. 1 to FIG. 3, an electron transport region ETR is provided on an emission layer EML. The electron transport region ETR may include at least one of an hole blocking layer HBL, an electron transport layer ETL, and an electron injection layer EIL. However, embodiments of the present disclosure are not limited thereto.

The electron transport region ETR may have a single layer formed using a single material, a single layer formed using a plurality of different materials, or a multilayer structure having a plurality of layers formed using a plurality of different materials.

For example, the electron transport region ETR may have a single layer structure of an electron injection layer EIL or an electron transport layer ETL, or a single layer structure formed using an electron injection material and an electron transport material. In some embodiments, the electron transport region ETR may have a single layer structure having a plurality of different materials, or a structure stacked from the emission layer EML of electron transport layer ETL/ electron injection layer EIL, or hole blocking layer HBL/ electron transport layer ETL/electron injection layer EIL, without limitation. The thickness of the electron transport region ETR may be, for example, about 1,000 Å to about 1,500 Å.

The electron transport region ETR may be formed using any suitable method (such as a vacuum deposition method, a spin coating method, a cast method, a Langmuir-Blodgett (LB) method, an inkjet printing method, a laser printing method, and/or a laser induced thermal imaging (LITI) method).

When the electron transport region ETR includes an electron transport layer ETL, the electron transport region ETR may include an anthracene-based compound. The electron transport region may include, for example, tris(8-hydroxyquinolinato)aluminum (Alq$_3$), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzimidazolyl-1-ylphenyl)-9,10-dinaphthylanthracene, 1,3,5-tri(1-phenyl-1H-benz[d]imidazol-2-yl)phenyl (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1, O8)-(1,1'-biphenyl-4-olato) aluminum (BAlq), beryllium bis(benzoquinolin-10-olate (Bebq$_2$), 9,10-di(naphthalene-2-yl)anthracene (ADN), or any mixture thereof, without limitation.

The thickness of the electron transport layer ETL may be about 100 Å to about 1,000 Å, for example, about 150 Å to about 500 Å. When the thickness of the electron transport layer ETL satisfies the above-described range, satisfactory electron transport properties may be obtained without substantial increase of a driving voltage.

When the electron transport region ETR includes the electron injection layer EIL, the electron transport region ETR may include a metal halide (such as LiF, NaCl, CsF, RbCl, Rbl, and/or CuI), a lanthanide metal (such as ytterbium (Yb)), or a metal oxide (such as Li$_2$O and/or BaO), or lithium quinolate (LiQ).

However, an embodiment of the present disclosure is not limited thereto. The electron injection layer EIL may also be formed using a mixture material of an electron transport material and an insulating organometal salt. The organometal salt may be a material having an energy band gap of about 4 eV or more. For example, the organometal salt may include, for example, metal acetates, metal benzoates, metal acetoacetates, metal acetylacetonates, and/or metal stearates. The thickness of the electron injection layer EIL may be about 1 Å to about 100 Å, and about 3 Å to about 90 Å. When the thickness of the electron injection layer EIL satisfies the above described range, satisfactory electron injection properties may be obtained without inducing substantial increase of a driving voltage.

The electron transport region ETR may include a hole blocking layer HBL as described above. The hole blocking layer HBL may include, for example, at least one of 2,9-dimethyl-4,7-diphenyl-1,10-phenanthroline (BCP), or 4,7-diphenyl-1,10-phenanthroline (Bphen). However, embodiments of the present disclosure are not limited thereto.

The second electrode EL2 is provided on the electron transport region ETR. The second electrode EL2 may be a common electrode or a cathode. The second electrode EL2 may be a transmissive electrode, a transflective electrode or a reflective electrode. When the second electrode EL2 is a transmissive electrode, the second electrode EL2 may include a transparent metal oxide, for example, ITO, IZO, ZnO, ITZO, etc.

When the second electrode EL2 is a transflective electrode or a reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, Yb, W, In, Sn, Zn, a compound thereof, a mixture thereof (for example, a mixture of Ag and Mg), or and oxide thereof. The second electrode EL2 may have a multilayered structure including a reflective layer or a transflective layer formed using the above-described materials and a transparent conductive layer formed using ITO, IZO, ZnO, ITZO, etc.

In some embodiments, the second electrode EL2 may be connected with an auxiliary electrode. When the second electrode EL2 is connected with the auxiliary electrode, the resistance of the second electrode EL2 may decrease.

In some embodiments, the organic light emitting device 10 of an embodiment may further include a buffer layer between an emission layer EML and an electron transport region ETR. The buffer layer may control the concentration of excitons produced in the emission layer EML. For example, the buffer layer may include a portion of the materials of the emission layer EML. The buffer layer may include a host material among the materials of the emission layer EML. The material of the buffer layer may be selected to have a lowest triplet excitation energy level greater than or equal to the lowest triplet excitation energy level of the second dopant and less than or equal to the lowest triplet excitation energy level of the first dopant according to the combination of the host and dopant materials.

The organic light emitting device 10 according to an embodiment of the present disclosure may include the crosslinking agent compound of an embodiment in a hole transport region HTR disposed between the first electrode EL1 and the second electrode EL2, and an organic light emitting device having high emission efficiency and a low driving voltage may be provided through the increase of the residual layer properties of the hole transport region HTR by forming the hole transport region through a wetting process such as ink jet printing.

Figure 4A:
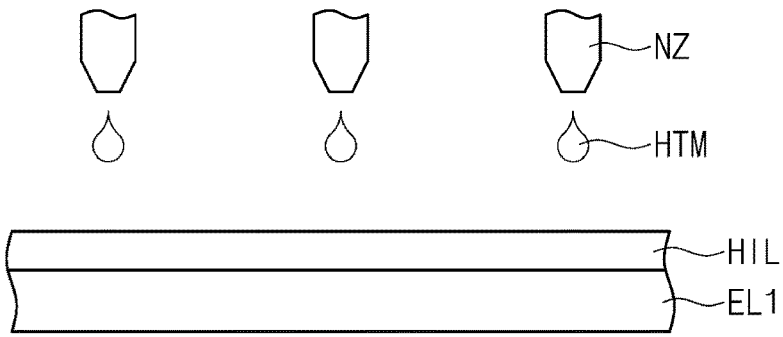
FIGS. 4A to 4C are cross-sectional views schematically illustrating a partial step among the method for manufacturing an organic light emitting device according to an embodiment of the present disclosure.
Figure 4B:
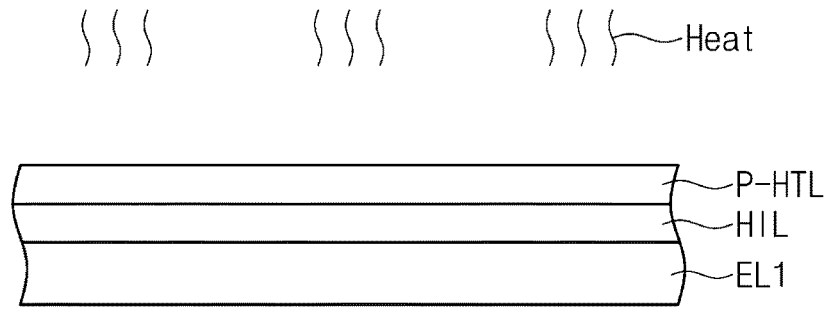
Figure 4C:
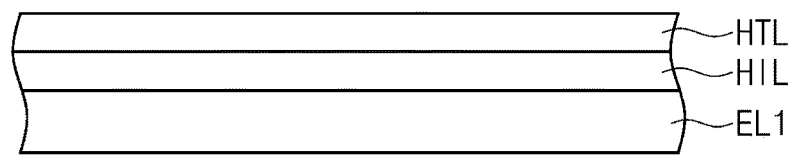

FIGS. 4A to 4C are cross-sectional views schematically showing partial steps of the manufacturing method of the organic light emitting device according to an embodiment of the present disclosure. In FIGS. 4A to 4C, a step of forming a hole transport layer HTL on a hole injection layer HIL in the manufacturing method of the organic light emitting device according to an embodiment of the present disclosure is shown step by step. Hereinafter, the method of manufacturing the organic light emitting device according to an embodiment of the present disclosure will be explained referring to FIGS. 4A to 4C.

The method of manufacturing the organic light emitting device according to an embodiment includes a step of preparing a first electrode, a step of forming a hole transport region by providing a hole transport material on the first electrode, a step of forming an emission layer on the hole transport region, and a step of forming a second electrode on the emission layer.

Referring to FIGS. 4A to 4C, a hole transport region HTR (see FIG. 1) includes a hole injection layer HIL formed on a first electrode EIJ1, and a hole transport layer HTL formed on the hole injection layer HIL, and the hole transport layer HTL may be formed through a hole transport material HTM. The hole transport material HTM may include the crosslinking agent compound of an embodiment. The hole transport material HTM may include the crosslinking agent compound represented by Formula 1. The hole transport material HTM may further include a polymer compound including a substituted or unsubstituted triarylamine group, and the polymer compound may be represented by Formula 2-1 or Formula 2-2. In the hole transport material HTM, the weight ratio of the polymer compound and the crosslinking agent compound may be about 4:1 to about 19:1. For example, the weight ratio of the polymer compound and the crosslinking agent compound in the hole transport material HTM may be about 9:1. The hole transport material HTM may be prepared by mixing the polymer compound and the crosslinking agent compound in a solvent. In an embodiment, the solvent may include each of toluene, xylene, o-xylene, m-xylene or anisole, or any combination thereof (e.g., as a mixed solvent).

The hole transport material HTM may be deposited on the hole injection layer HIL through a wetting process. FIG. 4A illustrates an example embodiment of supplying a hole transport material HTM through nozzles NZ on a hole injection layer HIL. However, the hole transport material HTM may be deposited using any suitable solution process technique, including spin coating, ink jet printing, nozzle printing and spray printing, without limitation.

The method of manufacturing an organic light emitting device according to an embodiment may include, after supplying the hole transport material HTM on the hole injection layer HIL to form a preliminary hole transport layer P-HTL, a step of forming a hole transport layer HTL by applying heat or light on the preliminary hole transport layer P-HTL. FIG. 4B illustrates an example embodiment on the formation of a hole transport layer HTL by thermally-crosslinking a polymer compound and a crosslinking agent compound included in the preliminary hole transport layer P-HTL, but an embodiment of the present disclosure is not limited thereto, and the hole transport layer HTL may be formed by photo-crosslinking the polymer compound and the crosslinking agent compound included in the preliminary hole transport layer P-HTL.

Hereinafter, the crosslinking agent compound according to an embodiment of the present disclosure, the polymer compound and the organic light emitting device of an embodiment will be particularly explained referring to embodiments and comparative embodiments. The following embodiments are only illustrations to assist the understanding of the present disclosure, and the scope of the present disclosure is not limited thereto.

EXAMPLES

1. Synthesis of Crosslinking Agent Compound

First, the method of synthesizing the crosslinking agent compound according to an embodiment will be explained in more detail referring to the synthetic methods of Example Compounds 1 and 2. The synthetic method of the crosslinking agent compound explained herein below is an embodiment, and the synthetic method of the crosslinking agent compound according to an embodiment of the present disclosure is not limited thereto. The structures of Example Compounds 1 and 2 are as follows:

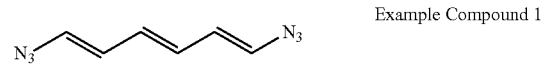

Example Compound 1

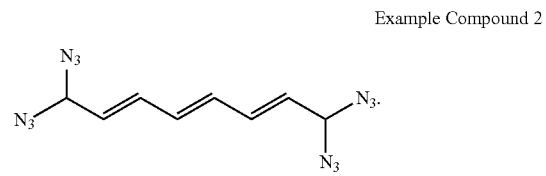

Example Compound 2

(1) Synthesis of Example Compound 1

Example Compound 1 according to an embodiment was synthesized by a method below.

The chlorine atoms of 1,6-dichlorohexa-1,3,5-triene were substituted with azide groups through a nucleophilic substitution reaction to obtain Example Compound 1. In a flask under nitrogen atmosphere, 1,6-dichlorohexa-1,3,5-triene (10.0 g, 0.067 mol) and sodium azide (10.5 g, 0.161 mol, 2.4 eq) were dissolved in a DMF solvent and stirred at room temperature for about 12 hours to synthesize Example Compound 1 in a yield of 95%.

(2) Synthesis of Example Compound 2

Example Compound 2 according to an embodiment was synthesized by a method below.

The chlorine atoms of 1,1,8,8-tetrachlorohexa-2,4,6-triene were substituted with azide groups through a nucleophilic substitution reaction to obtain Example Compound 2. In a flask under nitrogen atmosphere, 1,1,8,8-tetrachlorohexa-2,4,6-triene (10 g, 0.040 mol) and sodium azide (12.5 g, 0.192 mol, 4.8 eq) were dissolved in a DMF solvent and stirred at room temperature for about 12 hours to synthesize Example Compound 2 in a yield of 89%.

2. Preparation of Polymer Compound

In the crosslinking agent compound according to this embodiment, commercially available materials were used as Polymer Compounds A to C. The structures of Polymer Compounds A to C are as follows. In the compounds below, $q_1$ and $q_2$ are each independently an integer of 10 to 50.

Polymer Compound A

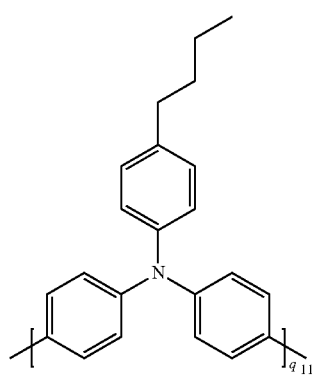

Polymer Compound B

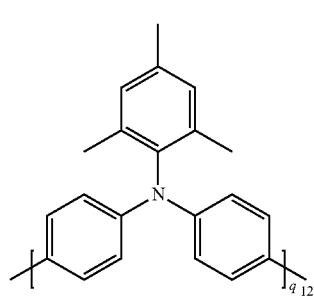

Polymer Compound C

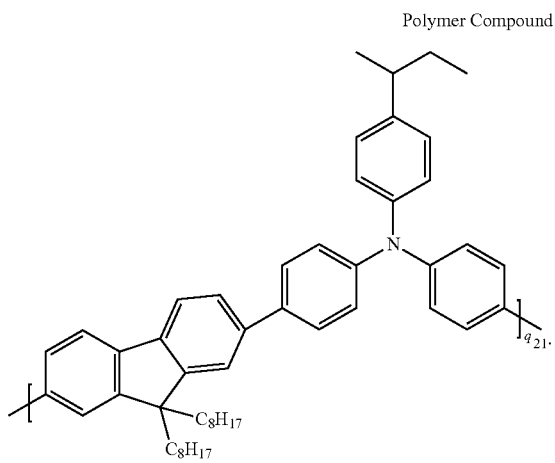

3. Evaluation of Residual Layer Properties

Each of the crosslinking agent compounds and each of the polymer compounds of the Examples and the Comparative Examples were mixed to form an ink, a single layer was formed through the ink, and the residual layer ratio of the single layer was measured. The combination of the crosslinking agent compound and the polymer compound used in each ink and a method of preparing the ink are as follows.

Example Ink 1 194765/411598

Example Compound 1 was used as the crosslinking agent compound, and Polymer Compound A was used as the polymer compound. After mixing Polymer Compound A and Example Compound 1 in a weight ratio of about 9:1, Example Ink 1 having a concentration of about 1.5% was prepared using anisole as a solvent.

Example Ink 2

Example Ink 2 having a concentration of about 1.5% was prepared via the same preparation method of Example Ink 1, except for using Example Compound 2 as the crosslinking agent compound.

Example Ink 3

Example Ink 3 having a concentration of about 1.5% was prepared via the same preparation method of Example Ink 1, except for using Polymer Compound B as the polymer compound.

Example Ink 4

Example Ink 4 having a concentration of about 1.5% was prepared via the same preparation method of Example Ink 3, except for using Example Compound 2 as the crosslinking agent compound.

Example Ink 5

Example Ink 5 having a concentration of about 1.5% was prepared via the same preparation method of Example Ink 1, except for using Polymer Compound C as the polymer compound.

Example Ink 6

Example Ink 6 having a concentration of about 1.5% was prepared via the same preparation method of Example Ink 5, except for using Example Compound 2 as the crosslinking agent compound.

Comparative Ink 1

Comparative Compound 1 was used as the crosslinking agent compound, and Polymer Compound A was used as the polymer compound. After mixing Polymer Compound A and Comparative Compound 1 in a weight ratio of about 9:1, Comparative Ink 1 having a concentration of about 1.5% was prepared using anisole as a solvent.

Comparative Ink 2

Comparative Ink 2 having a concentration of about 1.5% was prepared via the same preparation method of Comparative Ink 1, except for using Polymer Compound B as the polymer compound.

Example Compound 1

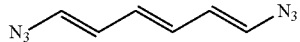

Example Compound 2

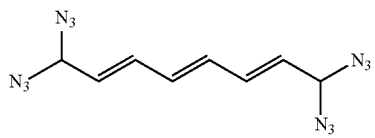

Polymer Compound A

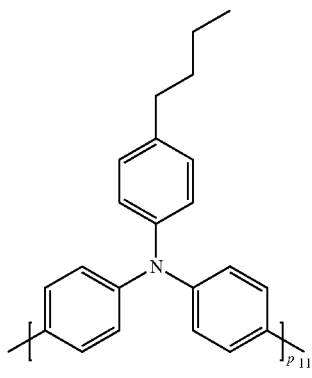

Polymer Compound B

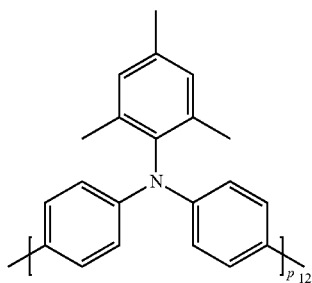

Polymer Compound C

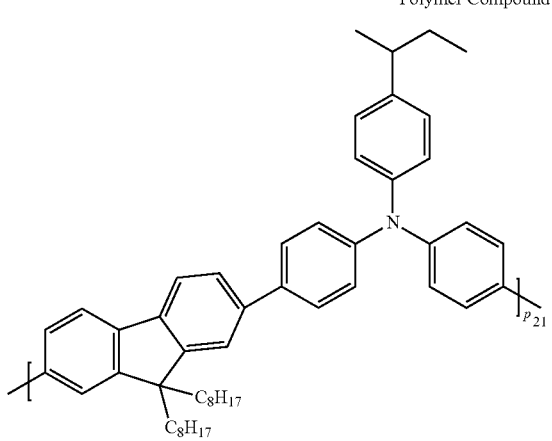

Comparative Compound 1

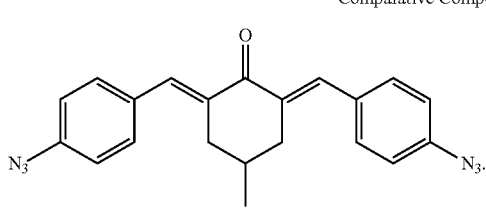

Formation of Single Layer and Evaluation of Residual Layer Ratio

Each of the inks of the Examples and Comparative Examples prepared above was supplied to form a layer having a thickness of about 400 Å, and dried at about 200° C. for about 30 minutes to complete the formation of a single layer. The UV of a corresponding single layer was measured first. Then, 50 microliters of methyl benzoate was dropped on the top of the corresponding single layer and allowed to stand for about 30 minutes. Then, the solvent was absorbed by a wipe, a thin film was dried at about 100° C. for about 1 minute, and UV was measured secondly. The residual layer ratio of the single layer (e.g., a ratio of the area of the layer remaining) was calculated through Equation 1:

Residual layer ratio (%)=second UV measurement area/first UV measurement area       Equation 1

The residual layer ratios of the single layers formed using Example Inks 1 to 6 and Comparative Inks 1 and 2 were evaluated and are shown in Table 1.

TABLE 1

| Ink composition | Crosslinking agent compound | Polymer Compound | Residual layer ratio (%) |
| --- | --- | --- | --- |
| Example Ink 1 | Example Compound 1 | Polymer Compound A | 100 |
| Example Ink 2 | Example Compound 2 | Polymer Compound A | 100 |
| Example Ink 3 | Example Compound 1 | Polymer Compound B | 100 |
| Example Ink 4 | Example Compound 2 | Polymer Compound B | 100 |
| Example Ink 5 | Example Compound 1 | Polymer Compound C | 100 |
| Example Ink 6 | Example Compound 2 | Polymer Compound C | 100 |
| Comparative Ink 1 | Comparative Compound 1 | Polymer Compound A | 20 |
| Comparative Ink 2 | Comparative Compound 1 | Polymer Compound B | 10 |

Referring to the results of Table 1, it could be confirmed that the single layers formed by including the crosslinking agent compound according to an embodiment of the present disclosure each had a higher residual layer ratio than the single layer formed by including the crosslinking agent compound of the Comparative Examples.

The single layer including the crosslinking agent compound according to an embodiment had improved layer forming properties due to the crosslinking efficiency of the crosslinking agent compound, and because the conjugation properties of a polymer compound having hole transport capacity should not be not deteriorated by the crosslinking agent compound, an organic light emitting device having high emission efficiency and a low driving voltage may be manufactured.

The organic light emitting device of an embodiment may show a low driving voltage and improved device properties with high efficiency.

The crosslinking agent compound of an embodiment may be used in the forming process of the hole transport region of an organic light emitting device, and may contribute to improved resolution and efficiency of the organic light emitting device.

As used herein, the terms "substantially," "about," and similar terms are used as terms of approximation and not as terms of degree, and are intended to account for the inherent deviations in measured or calculated values that would be recognized by those of ordinary skill in the art.

Any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

Although the example embodiments of the present disclosure have been described, it is understood that the present disclosure should not be limited to these example embodiments, but various changes and modifications can be made by one ordinary skilled in the art within the spirit and scope of the present disclosure as set forth in the following claims and their equivalents.

What is claimed is:

1. An organic light emitting device, comprising:
a first electrode;
a hole transport region on the first electrode;
an emission layer on the hole transport region;
an electron transport region on the emission layer; and
a second electrode on the electron transport region,
wherein the hole transport region is derived from a hole transport material comprising a crosslinking agent compound represented by Formula 1:

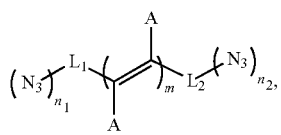

Formula 1 and
wherein in Formula 1, A is a hydrogen atom or a deuterium atom,
$L_1$ and $L_2$ are each independently a direct linkage or a substituted or unsubstituted methylene group,
"m" is an integer of 1 to 100, and
"$n_1$" and "$n_2$" are each independently 1 or 2.

2. The organic light emitting device of claim 1, wherein the hole transport region comprises:
a hole injection layer on the first electrode; and
a hole transport layer on the hole injection layer, and
wherein the hole transport layer is derived from the hole transport material comprising the crosslinking agent compound represented by Formula 1.

3. The organic light emitting device of claim 1, wherein the hole transport region comprises a plurality of organic layers, and
wherein an organic layer adjacent to the emission layer among the plurality of organic layers is derived from the hole transport material comprising the crosslinking agent compound represented by Formula 1.

4. The organic light emitting device of claim 1, wherein the crosslinking agent compound represented by Formula 1 is represented by Formula 1-1 or Formula 1-2:

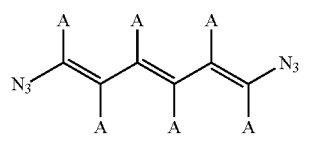

Formula 1-1

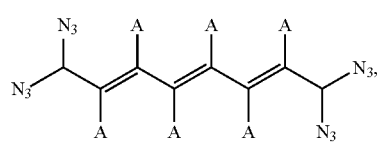

Formula 1-2 and
wherein in Formula 1-1 and Formula 1-2, A is the same as defined in Formula 1.

5. The organic light emitting device of claim 1, wherein the hole transport material further comprises a polymer compound comprising a substituted or unsubstituted triarylamine group.

6. The organic light emitting device of claim 5, wherein the polymer compound is represented by Formula 2-1 or Formula 2-2:

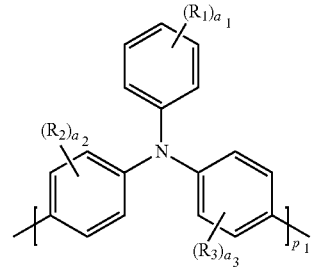

Formula 2-1

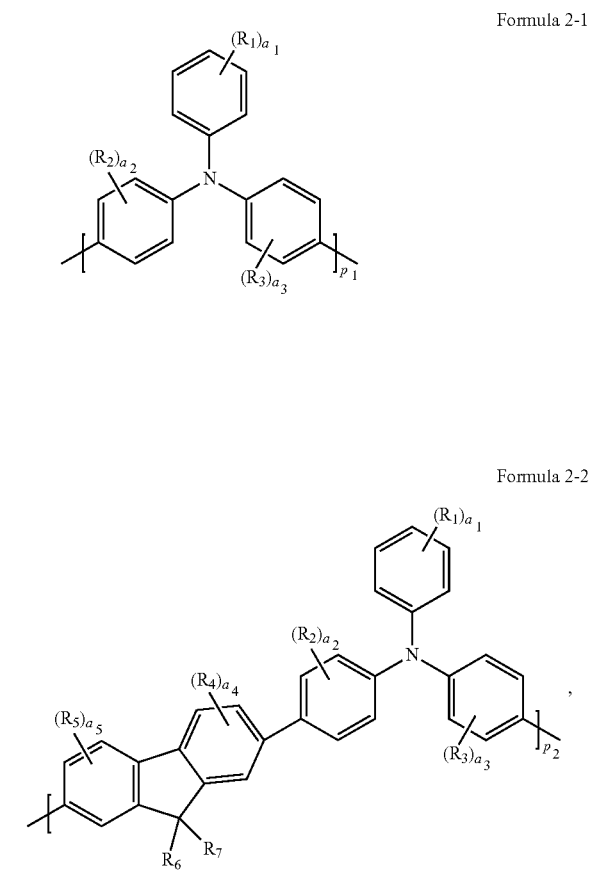

Formula 2-2 and
wherein in Formula 2-1 and Formula 2-2,
$R_1$ to $R_7$ are each independently a hydrogen atom, a deuterium atom, a halogen atom, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring,
"$a_1$" is an integer of 0 to 5,
"$a_2$" and "$a_3$" are each independently an integer of 0 to 4,
"$a_4$" and "$a_5$" are each independently an integer of 0 to 3, and
"$p_1$" and "$p_2$" are each independently an integer of 1 to 100.

7. The organic light emitting device of claim 6, wherein the polymer compound is represented by any one selected from Formula 2-1-1, Formula 2-1-2, and Formula 2-2-1:

Formula 2-1-1

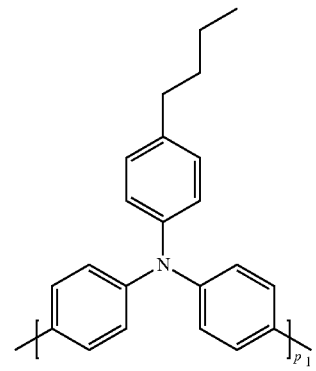

Formula 2-1-2

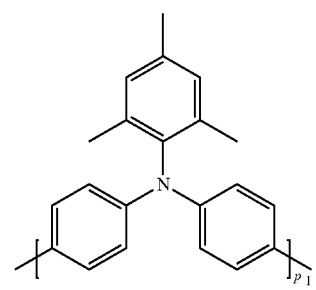

Formula 2-2-1

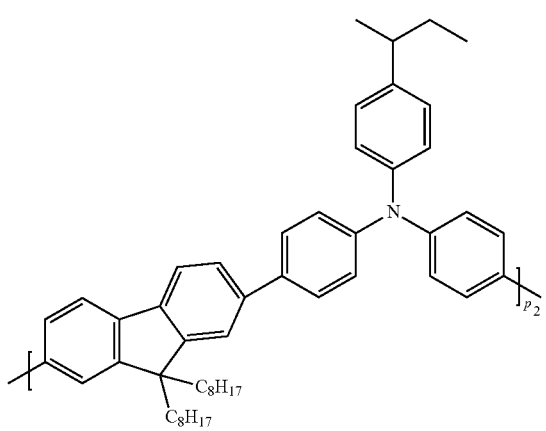

and wherein in Formula 2-1-1, Formula 2-1-2 and Formula 2-2-1,

"$p_1$" and "$p_2$" are the same as defined in Formula 2-1 and Formula 2-2.

8. The organic light emitting device of claim 5, wherein a weight ratio of the polymer compound and the crosslinking agent compound comprised in the hole transport material is about 4:1 to about 19:1.

9. The organic light emitting device of claim 5, wherein, in the hole transport region, the polymer compound is thermally-crosslinked or photo-crosslinked with the crosslinking agent compound.

10. A crosslinking agent compound represented by Formula 1:

Formula 1

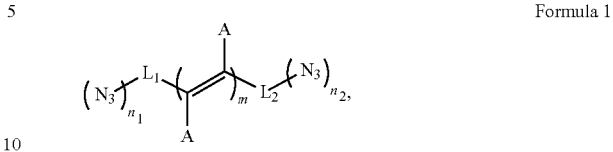

wherein in Formula 1,
A is a hydrogen atom or a deuterium atom,
"m" is an integer of 1 to 100,
$L_1$ and $L_2$ are each independently a direct linkage or a substituted or unsubstituted methylene group, and
"$n_1$" and "$n_2$" are each independently 1 or 2.

11. The crosslinking agent compound of claim 10, wherein the crosslinking agent compound represented by Formula 1 is represented by Formula 1-1 or Formula 1-2:

Formula 1-1

Formula 1-2

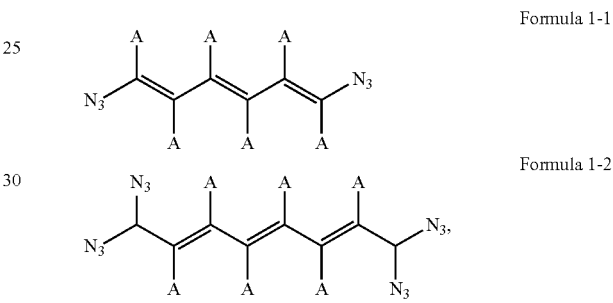

and wherein in Formula 1-1 and Formula 1-2, A is the same as defined in Formula 1.

12. A method of manufacturing an organic light emitting device, the method comprising:
preparing a first electrode;
supplying a hole transport material on the first electrode to form a hole transport region;
forming an emission layer on the hole transport region; and
forming a second electrode on the emission layer,
wherein the hole transport material comprises a crosslinking agent compound represented by Formula 1:

Formula 1

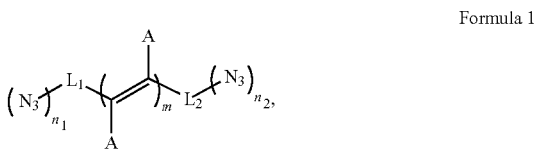

and wherein in Formula 1,
A is a hydrogen atom or a deuterium atom,
"m" is an integer of 1 to 100,
$L_1$ and $L_2$ are each independently a direct linkage, or a substituted or unsubstituted methylene group, and
"$n_1$" and "$n_2$" are each independently 1 or 2.

13. The method of manufacturing an organic light emitting device of claim 12, wherein the hole transport region comprises:
   a hole injection layer formed on the first electrode; and
   a hole transport layer formed on the hole injection layer, and
   wherein the hole transport layer is formed utilizing the hole transport material.

14. The method of manufacturing an organic light emitting device of claim 12, wherein the crosslinking agent compound represented by Formula 1 is represented by Formula 1-1 or Formula 1-2:

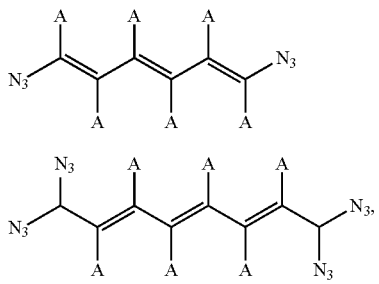

Formula 1-1

Formula 1-2 and
   wherein in Formula 1-1 and Formula 1-2, A is the same as defined in Formula 1.

15. The method of manufacturing an organic light emitting device of claim 12, wherein the hole transport material further comprises a polymer compound comprising a substituted or unsubstituted triarylamine group.

16. The method of manufacturing an organic light emitting device of claim 15, wherein the polymer compound is represented by Formula 2-1 or Formula 2-2:

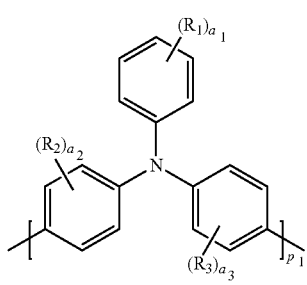

Formula 2-1

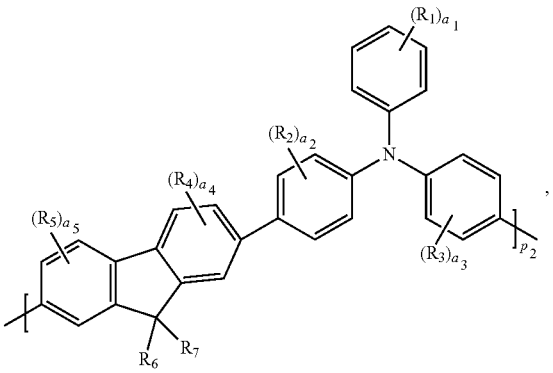

Formula 2-2 and
   wherein in Formula 2-1 and Formula 2-2,
   $R_1$ to $R_7$ are each independently a hydrogen atom, a deuterium atom, a halogen atom, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring,
   "$a_1$" is an integer of 0 to 5,
   "$a_2$" and "$a_3$" are each independently an integer of 0 to 4,
   "$a_4$" and "$a_5$" are each independently an integer of 0 to 3, and
   "$p_1$" and "$p_2$" are each independently an integer of 1 to 100.

17. The method of manufacturing an organic light emitting device of claim 15, wherein a weight ratio of the polymer compound and the crosslinking agent compound, comprised in the hole transport material is about 4:1 to about 19:1.

18. The method of manufacturing an organic light emitting device of claim 15, further comprising preparing the hole transport material by mixing the polymer compound, the crosslinking agent compound and a solvent, prior to supplying the hole transport material on the first electrode.

19. The method of manufacturing an organic light emitting device of claim 12, wherein the forming of the hole transport region further comprises curing the hole transport material supplied by applying heat or light, after supplying the hole transport material.

20. The method of manufacturing an organic light emitting device of claim 12, wherein the supplying of the hole transport material is performed through a wet process selected from spin coating, ink jet printing, nozzle printing, and spray printing.

* * * * *